United States Patent
Williams et al.

(10) Patent No.: US 6,285,030 B1
(45) Date of Patent: Sep. 4, 2001

(54) ARTICLE IRRADIATION SYSTEM IN WHICH ARTICLE TRANSPORTING CONVEYOR IS CLOSELY ENCOMPASSED BY SHIELDING MATERIAL

(75) Inventors: Colin Brian Williams, La Jolla; John Thomas Allen; George Michael Sullivan, Jr., both of San Diego, all of CA (US)

(73) Assignee: The Titan Corporation, San Diego, CA (US)

( * ) Notice: Subject to any disclaimer, the term of this patent is extended or adjusted under 35 U.S.C. 154(b) by 0 days.

(21) Appl. No.: 09/413,940

(22) Filed: Oct. 7, 1999

Related U.S. Application Data

(63) Continuation-in-part of application No. 08/854,202, filed on May 9, 1997, now Pat. No. 5,994,706.

(51) Int. Cl.$^7$ ................................................ G01N 21/00
(52) U.S. Cl. .................... 250/454.11; 250/453.11; 250/515.1; 378/69; 378/64
(58) Field of Search ................ 250/453.11, 455.11, 250/436, 515.1; 378/69, 64

(56) References Cited

U.S. PATENT DOCUMENTS

| | | | |
|---|---|---|---|
| 5,396,074 | * | 3/1995 | Peck et al. ................ 250/453.11 |
| 5,859,438 | * | 1/1999 | Nemezawa et al. ........... 250/519.1 |
| 6,051,185 | * | 4/2000 | Beers ............................. 422/22 |
| 6,127,687 | * | 10/2000 | Williams et al. ............. 250/492.3 |

* cited by examiner

Primary Examiner—Jack Berman
Assistant Examiner—Kalimah Fernandez
(74) Attorney, Agent, or Firm—Fulwider Patton, et al.; Ellsworth R. Roston

(57) ABSTRACT

Articles are transported by a conveyor system in a loop from a loading area past a target region to an unloading area adjacent the loading area. A first side of the article is irradiated by a radiation source in the target region during the article movement through the target region. The radiation source may be substantially parallel or perpendicular to the conveyor system. The loop has curved portions and straight portions between the curved portions. Radiation shielding material substantially fills the space within the loop. The conveyor system and the radiation source are disposed within a chamber made from a radiation shielding material (e.g. concrete). The shielding material inside and outside the loop defines a radiation-free loop portion having straight portions with a relatively close spacing. A bridge having no radiation shielding and a relatively short length is disposed in this radiation-free area as are the loading and unloading areas. The bridge rotates the articles through an 180° angle after the irradiation of the first side of the article and transfers the articles to the conveyor system at a position before the target region to obtain another movement of the articles past the radiation source and an irradiation of the second side of the articles. After such irradiation, the articles are transferred to the unloading area.

59 Claims, 5 Drawing Sheets

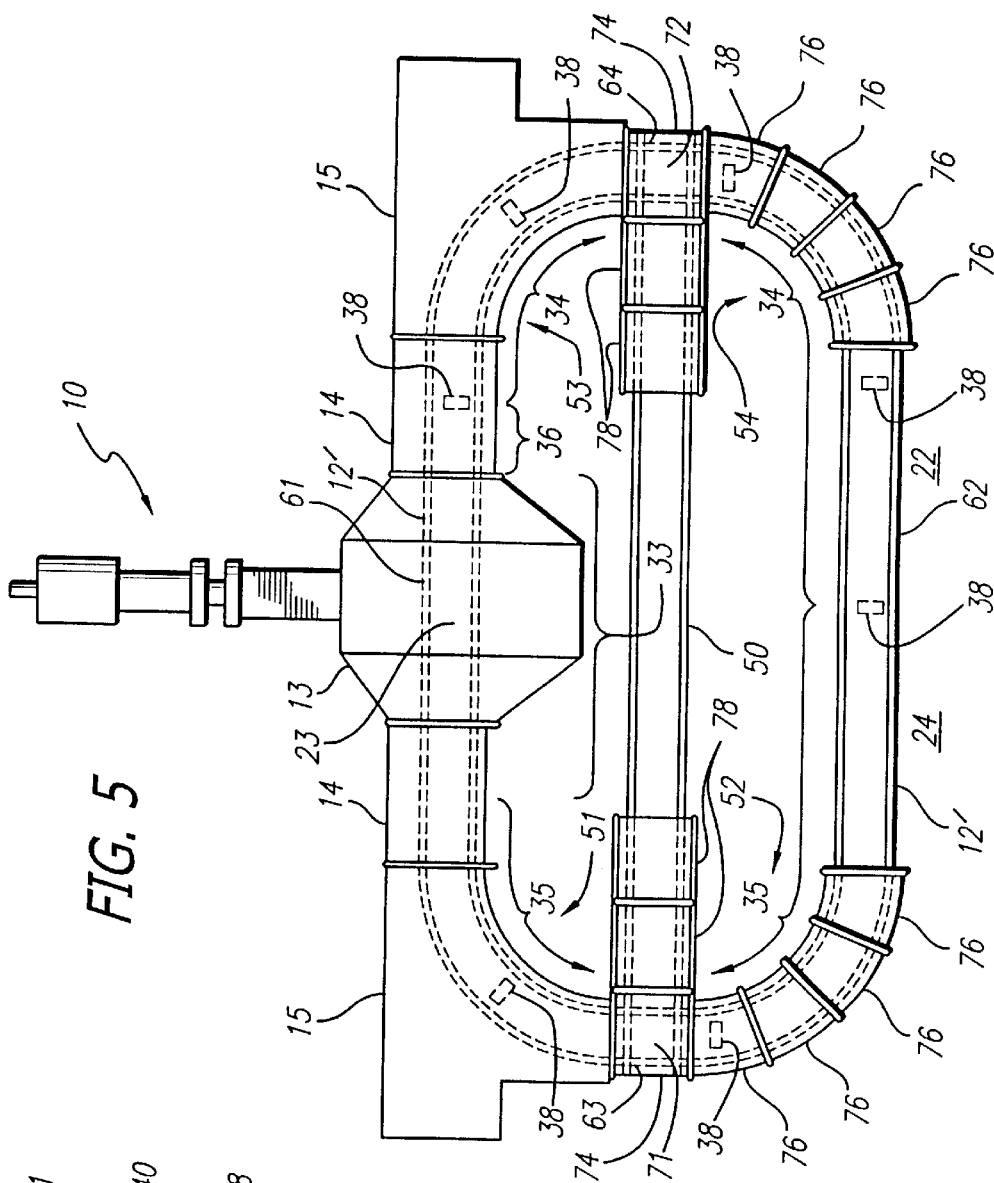
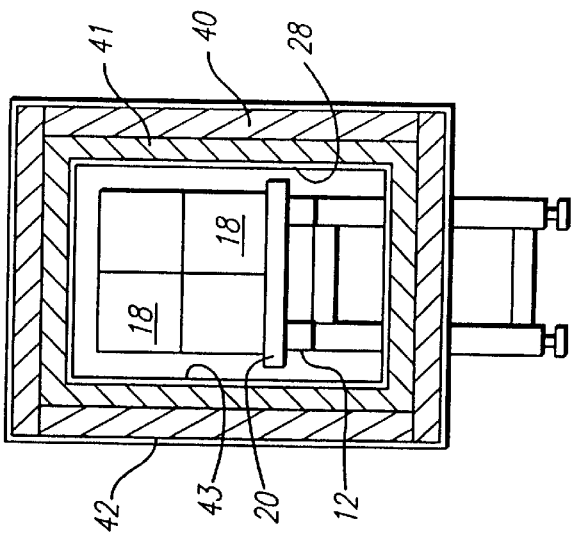
FIG. 5
FIG. 4

ARTICLE IRRADIATION SYSTEM IN WHICH ARTICLE TRANSPORTING CONVEYOR IS CLOSELY ENCOMPASSED BY SHIELDING MATERIAL

This application is a continuation-in-part of application Ser. No. 08/854,202 filed in the USPTO on May 9, 1997 now U.S. Pat. No. 5,994,706, by John Thomas Allen, George Michael Sullivan, Jr., Michael Scott Bresell, Harrold Brook Knowles, Anthony Alexander Zante, Richard Joseph Mendonsa, Richard Clarke Miller and Kenneth Whitham and assigned of record to the assignee of record of this application.

This invention relates to a system for, and method of, irradiating articles to sterilize the articles. The system and method of this invention are advantageous in that they provide for two (2) passes of the articles past a radiation source to irradiate the opposite sides of the articles and in that they provide a simplified bridging arrangement for rotating the article in the second pass through an angle of 180° to obtain the irradiation of the opposite side of the articles from the side of the article irradiated in the first pass. The system and method of this invention are also advantageous in providing improvements in shielding the articles to facilitate the construction of the simplified bridging arrangement without any radiation shielding in the simplified bridging arrangement.

BACKGROUND OF THE INVENTION

A prior art irradiation system that utilizes a conveyor system for transporting articles through a target region is described in U.S. Pat. No. 5,396,074 to Peck at el. U.S. Pat. No. 5,396,074 is assigned of record to the assignee of record of this application. In such prior art system, the radiation source and the conveyor system are disposed in a room having concrete walls, wherein such concrete walls and additional concrete walls defining an angled passageway to the room shield loading and unloading areas located outside of the room from radiation derived from the radiation source.

A system for reorienting the articles from retransportation through the target region also is described in U.S. Pat. No. 5,396,074 to Peck et al. In such reorienting system, a gear rack is disposed adjacent a reroute conveyor system (or bridging arrangement) that transports the articles from a position on a primary conveyor system located past the target region in the direction of movement of the primary conveyor system to a position on the primary conveyor system located before the target region in such direction of movement. A rotatable collar mechanism on an article carrier interacts with the gear rack in such a manner as the article carrier is being transported past the rack by the reroute conveyor system as to reorient the article carrier by 180 degrees.

In co-pending application 08/854,202 filed in the USPTO on May 9, 1997, and assigned of record to the assignee of record of this application, an article irradiation system is provided comprising a radiation source positioned for scanning a target region with radiation, a conveyor system for transporting articles from a loading area through the target region to an unloading area, and radiation shielding material defining a tunnel which closely encompasses portions of the conveyor system extending away from the target region toward the loading and unloading areas. By so disposing such closely encompassing radiation shielding material in order to shield the loading and unloading areas from radiation derived from the radiation source, an irradiation system is provided that requires a significantly less overall area than in the prior art.

For example, in the system of co-pending application Ser. No. 08/854,202 the conveyor system is disposed in a path having turns closely encompassed by the radiation shielding material and of such degree between the target region and the loading and unloading areas that the radiation shielding material closely encompassing said turns precludes a direct line of sight between the target region and the loading area and a direct line of sight between the target region and the unloading area. As a result, the loading and unloading areas in the system disclosed and claimed in co-pending application Ser. No. 08/854,202 are shielded from radiation derived from the radiation source. Such disposition facilitates a compact embodiment of the irradiation system in which the loading area and the unloading area are within a common unshielded area and the path of the conveyor system defines a closed loop from the loading area to the unloading area. Such disposition also facilitates a compact embodiment of the irradiation system in which the conveyor system is included in an assembly line having an unshielded loading area and an unshielded unloading area.

In a second aspect, the article irradiation system disclosed and claimed in co-pending application Ser. No. 08/854,202 comprises a radiation source positioned for scanning a target region with radiation and a first conveyor system for transporting articles from a loading area through the target region to an unloading area, with the first conveyor system being disposed in a closed-loop path. A first side of the article is irradiated by the radiation source during the movement of the articles by the first conveyor system through the target region. The system of co-pending application Ser. No. 08/854,202 further comprises a second conveyor system coupled to the first conveyor system for transporting the articles from a first position on the first conveyor system. The first position is past the target region and has a given alignment. The second position on the first conveyor system is before the target region and has an alignment that is 180° different than the given alignment. In this way, the articles transported by the first conveyor system are reoriented by 180° with respect to the path of the first conveyor system for retransportation through the target region. This causes a second side of the articles to be irradiated by the radiation source during a second movement of the articles through the target region.

For example, in an embodiment of the system in co-pending application Ser. No. 08/854,202, the path of the first conveyor system has four turns and a straight segment between each pair of adjacent turns. The target region is within a first straight segment of the first conveyor system. The loading and unloading areas are adjacent a second straight segment of the first conveyor system on the opposite side of the loop from the first straight segment. The first position on the first conveyor system is in a third straight segment which is between the two turns of the loop that are between the target region and the unloading area. And the second position on the first conveyor system is in a fourth straight segment which is between the two turns of the loop that are between the target region and the loading area. In such an arrangement, the second conveyor system may be so simple as to merely defined a straight path from the first position on the first conveyor system to the second position on the first conveyor system.

In a third aspect, the system of co-pending application 08/854,202 provides a set of shielding modules for use in an article irradiation system that includes a radiation source positioned for scanning a target region with radiation and a conveyor system for transporting articles through the target region. These shielding modules comprise radiation shielding material which define a tunnel for closely encompassing a portion of the conveyor system. Such shielding modules are particularly well suited for use in embodiments of the irradiation system according to the above-described first aspect described above in which the conveyor system is disposed in a path having turns. For example some of the modules may be curved for respectively encompassing segments of the conveyor system having an arc of curvature that is an integer divisor of ninety degrees.

In a fourth aspect, the system of co-pending application Ser. No. 08/854,202 provides a radiation shielding assembly for use in an irradiation system that includes an electron beam radiation source positioned for scanning articles with an electron beam disposed in a target region. The radiation shielding assembly may comprise a beam stop of material for absorbing electrons and for converting the energy of the absorbed electrons into gamma-rays that are emitted from the beam stop. The beam stop is disposed on the opposite side of the target region from the radiation source. The radiation shielding assembly may also comprise a radiation shield for absorbing radiation while inhibiting emission of neutrons beyond the shielding assembly. The radiation shield defines a corridor through which the electron beam is scanned for irradiating articles disposed in the target region and further defines a tunnel through which articles may be transported to and from the target region. The tunnel and the corridor communicate with each other. When the corridor is positioned to communicate with the target region, one side of the article passing through the tunnel is irradiated with the radiation from the source.

The beam stop is disposed within a recess in a portion of the radiation shield that defines a portion of the corridor on the opposite side of the target region from the target source. In this way, gamma rays emitted from the beam stop toward the radiation source but obliquely thereto are inhibited by said portion of the radiation shield from entering the tunnel.

BRIEF DESCRIPTION OF THE INVENTION

The system and method disclosed in this continuation-in-part application provide certain advantages over the system and method disclosed and claimed in application Ser. No. 08/854,202. For example, the reroute conveyor system (or the bridging arrangement) in this continuation-in-part application is disposed in a radiation-free area of the looped conveyor system and is provided with a simplified construction and a shortened path. The simplified and shortened construction of the reroute conveyor system is facilitated by an enhanced distribution of radiation shielding material in the conveyor system.

In one embodiment of the invention articles are transported by a conveyor system in a loop from a loading area past a target region to an unloading area adjacent the loading area. A first side of the article is irradiated by a radiation source in the target region during the article movement through the target region. The radiation source may be substantially parallel or perpendicular to the conveyor system.

The loop has curved portions and straight portions between the curved portions. Radiation shielding material substantially fills the space within the loop. The conveyor system and the radiation source are disposed within a chamber made from a radiation shielding material such as concrete. The shielding material inside and outside the loop defines a radiation-free loop portion having straight portions with a relatively close spacing.

A bridge having no radiation shielding and a relatively short length is disposed in this radiation-free loop portion as are the loading and unloading areas. The bridge rotates the articles through an 180° angle after the irradiation of the first side of the article and transfers the articles to the conveyor system at a position before the target region to obtain another movement of the articles by the conveyor system past the radiation source and an irradiation of the second side of the articles by the radiation source. After such irradiation, the articles are transferred to the unloading area.

BRIEF DESCRIPTION OF THE DRAWINGS

FIG. 4 is an end view of a preferred embodiment of a radiation shielding module which encompasses a portion of the conveyor system shown in FIGS. 1 and 3;

FIG. 5 is a plan view of another preferred embodiment of an irradiation system in which portions of the conveyor system encompassed by radiation shielding material are shown by dashed lines;

DETAILED DESCRIPTION

Figure 1:
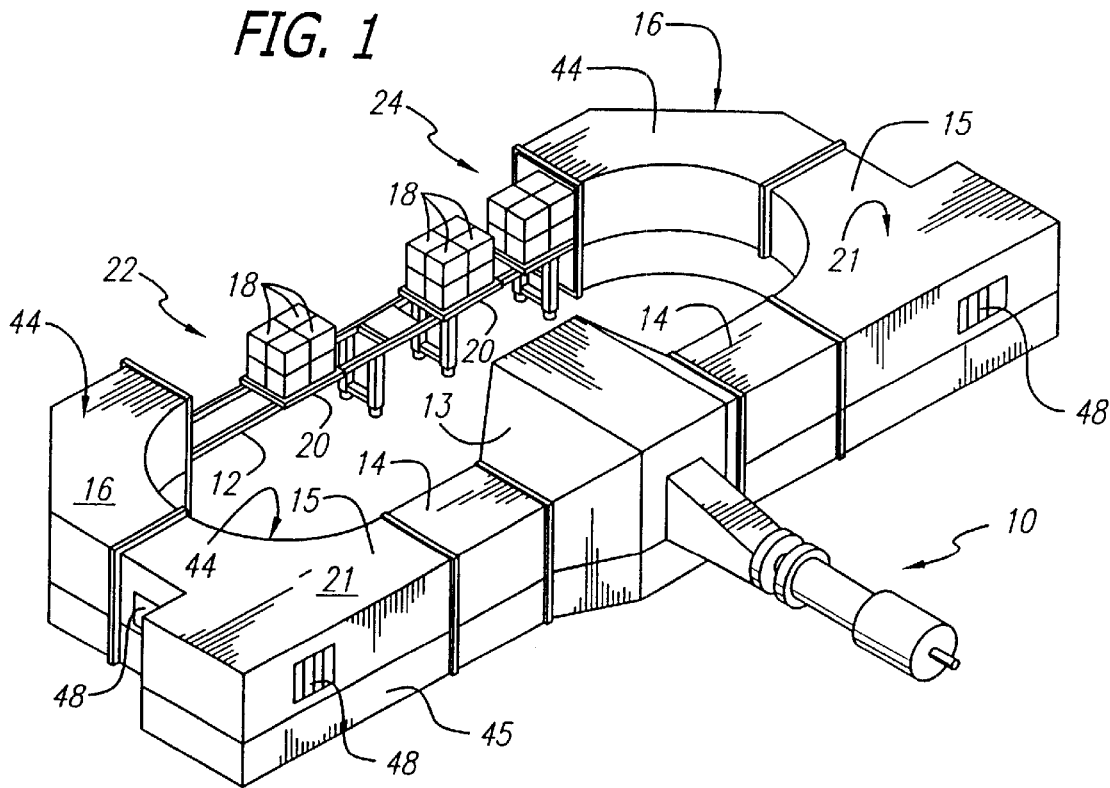
FIG. 1 is a perspective view of an embodiment of an irradiation system having features which are incorporated in this invention.
Figure 2:
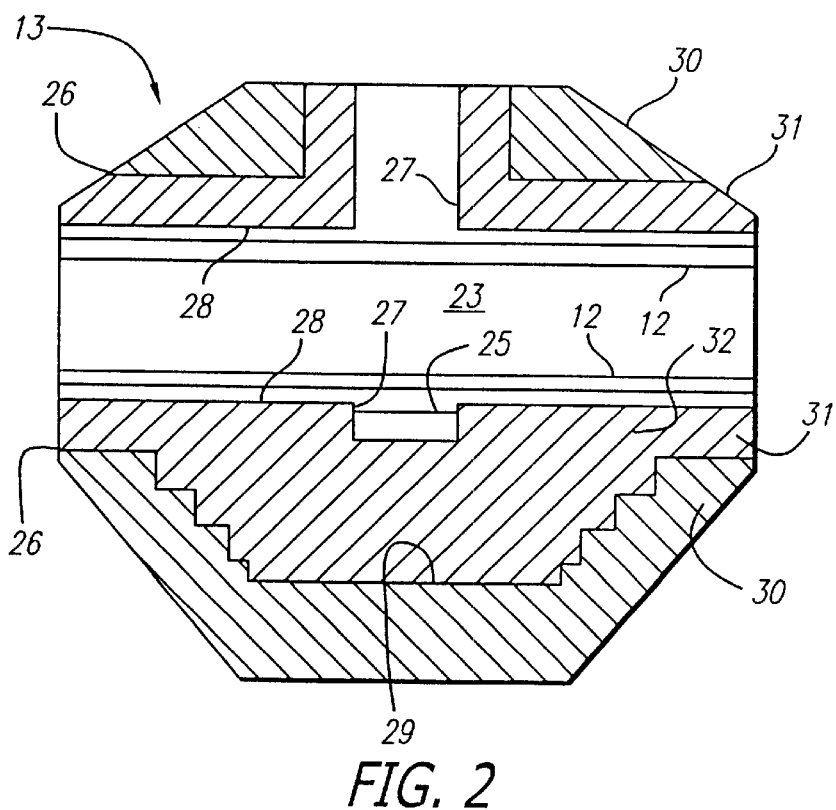
FIG. 2 is a diagram in section of the interior of a preferred embodiment of a radiation shielding assembly included in the irradiation system of FIG. 1.
Figure 3:
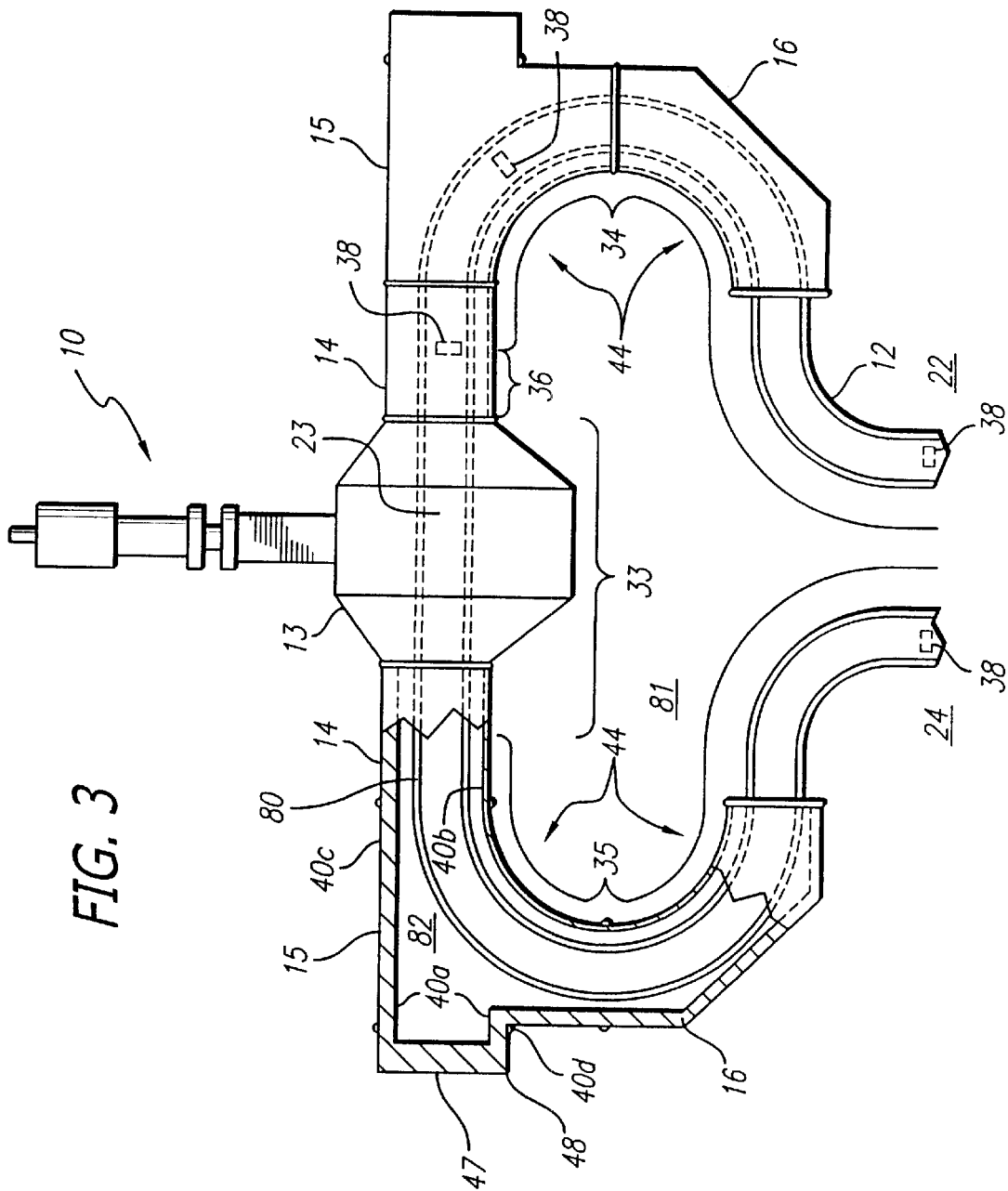
FIG. 3 is a plan view showing a modified embodiment, included within an assembly line, of the irradiation system of FIG. 1, portions of radiation shielding modules being broken away to show the disposition of the radiation shielding material therein in relation to the conveyor system. In the portions of the diagram of FIG. 3 in which portions of the radiation shielding modules are not broken away, the portions of the conveyor system encompassed by radiation shielding material are shown by dashed lines.

Referring to FIGS. 1, 2 and 3, a preferred embodiment of an irradiation system incorporating features included in the present invention is shown as having a radiation source generally indicated at 10, a conveyor system 12 and a radiation shielding assembly 13. The radiation system is also shown as having a pair of straight-section radiation shielding modules 14 respectively having one end sealed to opposite ends of the radiation shielding assembly 13, a first pair of corner-section radiation shielding modules 15 respectively having one end sealed to the other ends of the straight-section radiation shielding modules 14 and a second pair of corner-section radiation shielding modules 16 respectively having one end sealed to the other ends of the first pair of corner-section radiation shielding modules 15. Articles 18 (FIG. 1) carried by article carriers 20 are transported by the conveyor system 12 in a direction indicated by arrows 21 (FIG. 21) from a loading area 22 through a target region 23 to an unloading area 24. The radiation source 10 is positioned for scanning the target region 23 with radiation. As shown in FIGS. 1 and 3, the conveyor system 12 and the radiation source 10 are disposed in a common horizontal plane.

The radiation source 10 preferably is a 10-million-electron-volt linear accelerator having an electron accelerating wave guide that provides an electron beam for irradiating articles 18 transported through the target region 23 by the convey system 12. The radiation source 10 is disposed along an approximately horizontal axis outside a loop defined by the path of the conveyor system 12 and scans the articles 18 with an electron beam at a given rate in a plane perpendicular to the direction of transport by the conveyor system 12. The scanning height and the current of the electron beam are adjusted in accordance with the height and radiation absorption characteristics of the articles being scanned. The scanning of the articles 18 by the electron beam is further controlled as described in the above-referenced U.S. Pat. No. 5,396,074. The accelerator is located inside a removable shield and protected by interior walls from ionizing radiation and ozone. In alternative embodiments, the radiation source scans the articles with a type of radiation other than an electron beam, such as X-rays.

Referring to FIG. 2, the radiation shielding assembly 13 includes a beam stop 25 and a radiation shield 26. The radiation shield 26 includes material for absorbing radiation while inhibiting emission of neutrons beyond the shielding assembly 13. The radiation shield 26 defines a corridor 27 through which the electron beam is scanned for irradiating articles 18 disposed in the target region 23 and further defines a tunnel 28 through which the articles 18 may be transported by the conveyor system 12 to and from the target region 23. Preferably, the portion of the radiation shield 26 defining the tunnel 28 closely encompasses the conveyor system 12.

The beam stop 25 is disposed on the opposite side of the target region 23 from the radiation source 10 and includes a material, such as aluminum, for absorbing electrons and for converting the energy of the absorbed electrons into gamma-rays that are emitted from the beam stop 25. The beam stop is disposed within a recess 29 in a portion of the radiation shield 26 that defines a portion of the corridor 27 on the opposite side of the target region 23 from the radiation source 10 so that gamma-rays emitted from the beam stop 25 toward the radiation source 10 but obliquely thereto are inhibited from entering the tunnel 28 by such portion of the radiation shield 26.

The radiation shield 26 includes a layer of lead 30 for absorbing the emitted gamma-rays and a layer of cadmium-free iron 31 disposed between the lead 30 and the corridor 27 for reducing the velocity of the emitted gamma-rays so that gamma-rays entering the lead 30 from the iron 31 are absorbed by the lead 30 and do not cause neutrons to be emitted from the lead 30. The iron 31 is disposed within a recess 32 within the lead 30 in the portion of the radiation shield 26 that is on the opposite side of the target region 23 from the radiation source 10 so that gamma-rays emitted from the iron 31 toward the radiation source 10 but obliquely thereto are inhibited from entering the tunnel 28 by the lead 30 in such portion of the radiation shield 26. Both the lead portion 30 and the iron portion 31 of the radiation shield 26 are readily constructed with a plurality of plates of various dimensions having a thickness in a range of approximately three to six inches, a width in a range of approximately two to four feet and a length in a range of approximately two to six feet. In one alternative embodiment (not shown) the radiation shield 26 includes a much thicker layer of cadmium-free iron and does not include any lead.

In another alternative embodiment (not shown), the radiation shield 26 includes concrete for absorbing the emitted gamma-rays with the concrete replacing the lead 30 and the iron 31 in the space on the opposite side of the target region 23 from the radiation source 10 and extending toward the loading area 22 and the unloading area 24 by such distances and in such directions as are required to provide adequate shielding of the loading area 22 and the unloading area 24 from radiation derived from the radiation source 10.

The conveyor system 12 may preferably be a chain conveyor system constructed of Bosch TS 3 Modular Conveyor components available from Bosch Automation Products, Buchanan, Mich. The article carriers 20 may preferably be Bosch workpiece pallets.

FIG. 3 shows an embodiment of the irradiation system in which the conveyor system 12 is included within an assembly line. In one such embodiment, the loading area 22 is a packaging area of the assembly line and the unloading area 24 is a boxing area of the assembly line. In another such embodiment, the loading area 22 is a boxing area of the assembly line and the unloading area 24 is the end of the assembly line from which the boxed articles 18 are removed for shipping.

Still referring to FIG. 3, the conveyor system 12 includes a process conveyor section 33, an inbound transport conveyor section 34, an outbound transport conveyor section 35 and a closing conveyor section 36, all of which conveyor sections are independently powered. The process conveyor section 33 transports the article carriers 20 through the target region 23 at a first speed. The first inbound conveyor section 34 transports the article carriers 20 from the loading area 22 to the closing conveyor section 36 at a second speed that differs from the first speed.

The closing conveyor section 36 transports the article carriers 20 from the inbound transport conveyor section 34 to the processor conveyor section 33 at a speed that is varied during such transport to position the article carriers 20 on the process conveyor section 33 for providing a predetermined separation distance between adjacent positioned article carriers 20. The closing conveyor section 36 transports the article carriers 20 at the speed of the process conveyor section 33 when the closing conveyor section 36 positions the article carrier 20 on the processor conveyor section 33. The variable speed of the closing conveyor section 36 is controlled as described in the above-referenced U.S. Pat. No. 5,396,074.

The outbound transport conveyor section 35 transports the article carriers 20 from the process conveyor section 33 to the unloading area 24 at a speed that may be the same as or different from the second speed of the inbound transport conveyor section 34. When the conveyor system 12 defines a closed loop, as shown in FIG. 1, the inbound transport conveyor section 34 and the outbound transport conveyor section 35 may be combined into a single transport conveyor section that is driven at the second speed, or the inbound transport conveyor section 34 and the outbound transport conveyor section 35 may be driven separately at respective speeds that may be the same or different.

The construction and operation of the process conveyor section 33, the inbound transport conveyor section 34, the outbound transport conveyor section 35 and the closing conveyor section 36 are disclosed in additional detail in U.S. Pat. No. 5,396,074. Reference may be made to U.S. Pat. No. 5,396,074 to provide additional details concerning the construction and operation of the different conveyor sections specified above.

Stop gates 38 (FIGS. 1 and 3) are disposed at selected positions within the conveyor system 12, including before the closing conveyor section 36, in the loading area 22, in the unloading area 24, and within the inbound transport conveyor section 34 as shown, for queuing and traffic management of the article carriers 20.

Referring to FIG. 4, the radiation shielding modules 14, 15 and 16 include radiation shielding material, such as an outer layer of lead 40 surrounding an inner layer of cadmium-free iron 41 and disposed within a stainless-steel container 42. The exposed inner surface of the iron layer 41 is covered with stainless-steel sheets 43. In an alternative embodiment (not shown) the radiation shielding modules 14, 15 and 16 include a much thicker layer of cadmium-free iron and do not include any lead. The radiation shielding materials 40 and 41 within the radiation shielding modules 14, 15 and 16 define extensions of the tunnel 28 and closely encompass the portions of the conveyor system 12 that extend away from the target region 23 toward the loading area 22 and the unloading area 24. The radiation shielding modules 14, 15 and 16 have adequate interior heights to enable a reasonable quantity of articles 28 to be stacked upon an article carrier 20. The radiation shielding modules 14, 15 and 16 do not extend all the way to the floor upon which the conveyor system 12 is supported. A skirt 45 extends between the bottoms of the radiation shielding modules 14, 15 and 16 and the floor, as shown in FIG. 1.

Referring to FIG. 1, individual radiation shielding modules 14, 15 and 16 respectively include at least one section that is movable, such as a door 48, for enabling access to the portion of the conveyor system 12 that is encompassed by the respective radiation shielding modules 14, 15 and 16.

Referring further to FIGS. 1 and 3, the conveyor system 12 is disposed in a path having curved turns 44 that are closely encompassed by the radiation shielding materials 40 and 41 (FIG. 4) within the shielding modules 14 and are of such degree between the target region 23 and the loading and unloading areas 22 and 24 that the radiation shielding materials 40 and 41 closely encompassing the turns 44 preclude a direct line of sight between the target region 23 and the loading area 22 and a direct line of sight between the target region 23 and the unloading area 24, for thereby shielding the loading and unloading areas 22 and 24 from radiation derived from the radiation source 10. The closely encompassing radiation shielding materials 40 and 41 are so configured between the target region 23 and the loading and unloading areas 22 and 24 that radiation emanating from the target region 23 bounces off of the closely encompassing shielding materials 40 and 41 at least three times without there being a direct line of sight between a second bounce site and the loading area 22 or the unloading area 24.

The path of the conveyor system 12 extends from the loading area 22 to the curved turns 44 at the right end of FIG. 3, then extends along the curved turns 44 at the right end of FIG. 3, then extends in a straight segment or portion 80 between the curved turns at the right and left ends of FIG. 3, then extends along the curved turns 44 at the left end of FIG. 3 and then extends from the curved turn 44 at the left end of FIG. 3 to the unloading area 24 in FIG. 3. This path defines a loop (which may actually be considered to constitute a single loop). There is space within this path as indicated at 81. There is radiation shielding material 40b in this space. There is also space outside of this path as indicated at 82. The radiation shielding materials 40a, 40c and 40d define the limits of the space 82 outside of this path.

By disposing the conveyor system 12 in a path having curved turns 44, (a) the turns 44 may be and are of a continuous elevation so that lift-transverse units are not required in order to transport the article carriers 20 through such turns 44, and (b) elongated articles (not shown) extending beyond the front and/or rear of an article carriers 18 can be transported through a turn 44 that is closely encompassed by the radiation shielding materials 40 and 41.

At least some of the modules 16 are curved for respectively encompassing, in the conveyor system 12, segments having an arc of curvature that is an integer divisor of ninety degrees. In the embodiment of FIGS. 1 and 3 having two 180-degree turns 44 separated by straight segments, the second pair of corner-section shielding modules 16 are curved for encompassing 90-degree segments of the conveyor system 12.

Portions of the first pair of corner-section shielding modules 15 are adjacent the outside portions of the curved turns 44 of the conveyor system 12 that are within a direct line of sight from the target region 23. In these portions of the first pair of corner-section shielding modules 15, the radiation shielding material 40a in the space outside of the curved turn 44 is not as close to the path of the conveyor system 12 as the radiation shielding material 40b in the space inside of such curved turns 44. Furthermore, in these portions of the first pair of corner-section shielding modules 15, the radiation shielding material 40a in the space outside of the curved turns 44 is thicker than the radiation shielding material 40b in the space inside of the curved turns 44. The thicker radiation shielding material 40a in the space outside of the curved turns 44 that is within a direct line of sight from the target region 23 extends in a much thicker corner portion 47 to a far point 48 at a right angle from the radiation shielding material 40c that extends in a straight line to the target region 23. From the far point 48, the radiation shielding material 40d extends at a right angle from the much thicker corner portion 47 toward the path of the conveyor system 12. Although only the reference numerals 40a, 40b, 40c and 40d are used above in relation to the radiation shielding material adjacent the curved turns 44 within the first pair of corner-section radiation shielding modules 15, it is to be understood that the radiation shielding material 40a, 40b, 40c and 40d within the first pair of corner-section radiation shielding modules 15 includes both a layer of lead 40 and a layer of iron 41 as shown in FIG. 4.

In the portions of the first pair of corner-section shielding modules 15 that are adjacent the inside portions of the curved turns 44, the radiation shielding material 40b has approximately the same degree of curvature as the curved turns 44 in order to enhance dispersal of radiation reflected from the radiation shielding material 40b adjacent the outside portions of the curved turns 44 that are within a direct line of sight from the target region 23.

Referring to FIG. 5, in another preferred embodiment for use in reorienting the article carriers 20 by 180 degrees for retransportation through the target region 23 to thereby enable the articles 18 to be irradiated from first and second opposite sides, the irradiation system of the present invention includes a first conveyor system 12' for transporting the article carriers 20 through the target region 23 and a second conveyor system 50 coupled to the first conveyor system 12' for reorienting the article carriers 20 by 180 degrees with respect to the path of the first conveyor system 12'. This reorientation is provided for retransportation of the article carriers 20 through the target region 23 to obtain an irradiation of the second side of the articles 18 by the radiation source 10.

The path of the first conveyor system 12' in FIG. 5 defines a closed loop having four curved ninety-degree turns 51, 52, 53, 54 and a straight segment 61, 62, 63, 64 between each pair of adjacent turns. The target region 23 is within the first straight segment 61; the loading and unloading areas 22 and 24 are in a common unshielded area adjacent the second straight segment 62 on the opposite side of the loop from the first straight segment 61; the third straight segment 63 is between the two turns 51 and 52 of the loop that are between the target region 23 and the unloading area 24; and the fourth straight segment 64 is between the two turns 53 and 54 of the loop that are between the target region 23 and the loading area 22.

The second conveyor system 50 defines a straight path from a first position 71 in the third said straight segment 63 of the first conveyor system 12'. The first position 71 is past the target region 23. At the first position 71, the path of the first conveyor system 12' has a given alignment. The second conveyor system 71 defines a straight path 71 to a second position 72 in the fourth said straight segment 64 of the first conveyor system 12'. The second position 72 is before the target region 23. At the second position 72, the path of the first conveyor system 12' has an alignment that is one-hundred-and-eighty degrees different than the given alignment at the first position 71. The first conveyor system 12' includes lift-transverse units at the first and second positions 71 and 72 for effecting transfer of the article carriers 20 between the first conveyor system 12' and the second conveyor system 50.

By transporting the article carriers 20 from the first position 71 on the first conveyor system 12' to the second position 72 on the first conveyor system 12', the second conveyor system 50 reorients the articles 18 transported by the first conveyor system 12' by one-hundred-and-eighty degrees (180°) with respect to the path of the first conveyor system 12'. In this way, the second conveyor system provides for a retransportation of the articles 18 through the target region 23. In this retransportation of the articles 18 through the target region 23, the second side of the articles is irradiated with radiation from the radiation source 10.

The conveyor system 12' in the embodiment of FIG. 5 also includes a process conveyor section 33, an inbound transport conveyor section 34, an outbound transport conveyor section 35 and a closing conveyor section 36, which operate in the same manner as described with reference to the embodiment of FIG. 3.

The conveyor system 12' in the embodiment of FIG. 5 further includes stop gates 38 before the closing conveyor section 36, in the loading area 22, in the unloading area 24, and within the inbound transport conveyor section 34, the outbound transport conveyor section 35 and the second conveyor system 50, as shown, for queuing and traffic management of the article carriers 20.

The embodiment of the irradiation system shown in FIG. 5 also includes a radiation shielding assembly 13, a first pair of straight-section radiation shielding modules 14 respectively having one end sealed to opposite ends of the radiation shielding assembly 13, a first pair of corner-section radiation shielding modules 15 respectively having one end sealed to the other ends of the straight-section radiation shielding modules 14, as in the embodiment of FIGS. 1, 2 and 3, a second pair of straight radiation shielding modules 74 respectively having one end sealed to the other ends of the first pair of corner-section radiation shielding modules 15; a pair of sets of seriatim-sealed curved radiation shielding modules 76 sealed respectively to the other ends of the second pair of straight-section radiation shielding modules 74 and a pair of sets of seriatim-sealed straight radiation shielding modules 78 sealed respectively to the sides of the second pair of straight radiation shielding modules 74 that are adjacent the second conveyor system 50.

The curved shielding modules 76 are substantially similar to the second pair of curved corner-section shielding modules 16 shown in FIG. 3, except that the individual curved shielding modules 76 encompass shorter segments of the first conveyor system 12' than the segments of the first conveyor system 12 encompassed by the respective second pair of curved corner-section shielding modules 16 in the embodiments of FIGS. 1 and 3. The radiation shielding modules 14, 15, 74, 76 and 78 include radiation shielding material disposed in the same manner as shown in FIG. 4, except that in the second pair of straight radiation shielding modules 74, the side thereof that is sealed to an adjacent straight radiation module 78 has an opening into the adjacent straight radiation module 78. The radiation shielding material within the radiation shielding modules 14, 15, 74 and 76 define extensions of the tunnel 28 and closely encompass the portions of the first conveyor system 12' that extend away from the target region 23 toward the loading and unloading areas, 22 and 24, in order to preclude a direct line of sight between the target region 23 and the loading area 22 and a direct line of sight between the target region 23 and the unloading area 24. These portions of the first conveyor system 12' include the turns 51, 52, 53 and 54.

The radiation shielding material within the sets of seriatim-sealed straight radiation shielding modules 78 define tunnels branching off from the tunnel 28 and closely encompass those portions of the second conveyor system 50 that are adjacent the first and second positions 71 and 72 of the first conveyor system 12' where the second conveyor system 50 is coupled to the first conveyor system 12'. The tunnels 78 operate to shield the loading and unloading areas 22 and 24 from radiation derived from the radiation source 10. The interior side walls of the straight radiation shielding modules 78 may be a greater distance from the second conveyor system 50 than the interior side walls of the curved radiation shielding modules 76 are from the first conveyor system 12' in order to accommodate elongated articles extending beyond the front and/or rear of an article carrier 18.

The curved radiation shielding modules 76 respectively encompass twenty-two-and-one-half-degree segments of two of the ninety-degree turns 52 and 54 of the first conveyor system 12'. The individual curved radiation shielding modules 76 encompass approximately uniform-length segments of the first conveyor system 12'. The individual straight radiation shielding modules 78 encompass approximately uniform-length segments of the second conveyor system 50. In alternative embodiments, the curve shielding modules 76 encompass thirty-degree, forty-five-degree or ninety-degree segments of the two ninety-degree turns 52 and 54 of the first conveyor system 12'. For turns 44, 52 and 54 of the respective conveyor systems 12, 12' that are integer multiples of m degrees, the radiation shielding material 40 and 41 may be disposed within a plurality of curved radiation shielding modules 16 and 76 that respectively encompass m-degree segments of the turns. In other respects the irradiation system of FIG. 5 is substantially the same as the irradiation systems of FIGS. 1 and 3.

Shielding modules having an arc of curvature of less than ninety degrees are particularly useful for encompassing turns of conveyor systems that are other than ninety degrees. Although shielding modules having an arc of curvature of less than ninety degrees are more readily handled during assembly and disassembly of the irradiation system, shielding modules having a ninety-degree curvature usually are preferred because fewer shielding modules are thereby required in the overall irradiation system, whereby there are fewer sealed joints between the radiation shielding modules.

In an alternative embodiment, the radiation source 10 is disposed along an approximately vertical axis for scanning articles 18 transported through the target region 23 by the process conveyor section 33 and the radiation shielding assembly 13 is disposed about such vertical axis.

The dimensions of the various components of the radiation shielding assembly 13, and of the respective radiations shielding modules 14, 15, 16, 74, 75 at different locations within the irradiation system are determined by computer-aided modeling in accordance with a technique described in a manual entitled *"MCNP—A General Monte Carlo Code for Neutron and Photon Transport"* published by the Radiation Shielding Information Center, P.O. Box 2008, Oak Ridge, Tenn. 37831.

Figure 6:
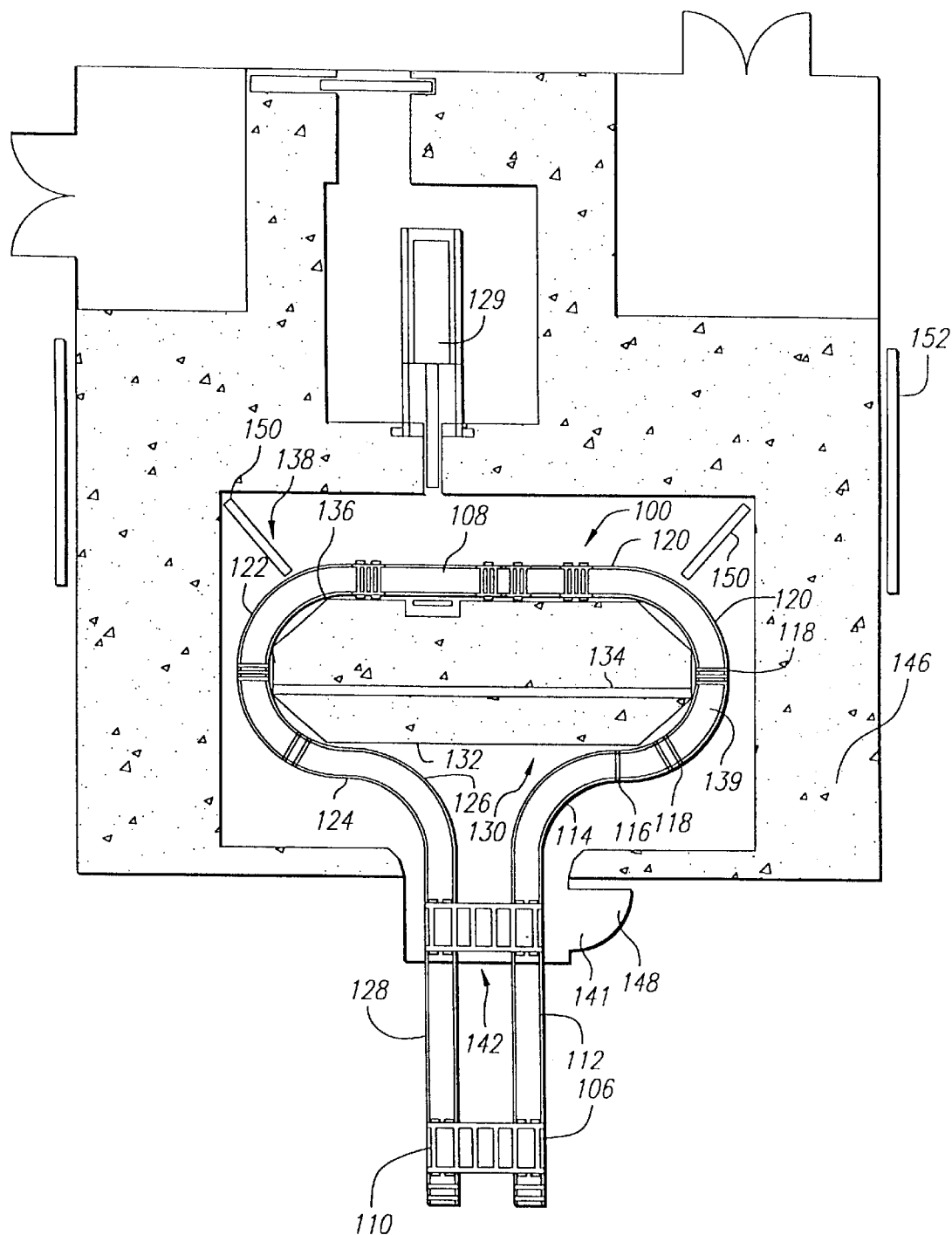
FIG. 6 is a plan view of a preferred embodiment of an irradiation system included within the scope of this invention and incorporating features shown in the previous Figures.

The embodiment shown in FIG. 6 includes a conveyor system, generally indicated at 100, having a path of movement similar to that shown in FIG. 3 and described above. The conveyor system 100 may be formed from a plurality of conveyors corresponding to the conveyors shown in FIGS. 3 and 4 and described above. The path of movement of article carriers (corresponding to the article carriers 20 in FIG. 1) for carrying articles may extend from a loading area 106 in a substantially closed loop past a target region 108 to an unloading area 110 disposed adjacent the loading area 106. The loading area 106 and the unloading area 110 may be considered to be disposed in substantially contiguous relationship to each other.

The closed loop includes a straight portion 112 extending from the loading area 106, a portion 114 having a substantially 90° curvature at the end of the straight portion 112, a straight portion 116 at the end of the curved portion 114, a portion 118 having a substantially 180° curvature (defined by two (2) connecting 90° curvatures) at the end of the straight portion 116, a straight portion 120 at the end of the 180° curved portion 118, a portion 122 having a substantially 180° curvature (defined by two (2) connecting 90° curvatures), a straight portion 124 at the end of the 180° curved portion 122, a portion 126 having a 90° curvature at the end of the straight portion 124 and a straight portion 128 at the end of the curved portion 126. The straight portions 112 and 128 are disposed close, and in substantially parallel relationship, to each other. The unloading area 106 is disposed near the end of the straight portion 128. Instead of providing the portion 118 with the substantially 180° curvature, the portion 118 may be defined by two (2) portions each with a 90° curvature and each separated from the other by a straight portion. This is also true of the portion 122 with the 180° curvature. The straight portions 112 and 128 may be considered to be in substantially contiguous relationship to each other.

As will be seen in FIG. 6, the conveyor system 100 is shaped in a loop to define a substantially confined space within the loop. A source 129 of radiation extends horizontally into the target region 108. Radiation shielding material generally indicated at 130 is disposed within this confined space to substantially fill the space. The radiation shielding material 130 may primarily constitute concrete 132. However, rods such as a rod 134 made from a suitable metal such as steel may be disposed within the concrete. The disposition of steel rods 134 within the concrete 132 is desirable because steel provides a greater shielding strength than concrete.

The concrete shielding 132 may be pointed at strategic positions in the concrete. For example, the concrete shielding may be pointed at a strategic position 136. This strategic position corresponds to a position at the juncture of the straight portion 120 and the curved portion 122. The pointed position 136 provides reinforcement in the concrete shielding 132 against the radiation which extends into the concrete shielding 132, from the juncture between the portions 120 and 122, in a direction indicated by an arrow 138. When the radiation extends into the radiation shielding material 132 in the direction 138 at the strategic position 136, the additional shielding material at the position 136 provides an additional shielding action against radiation.

A reroute conveyor system (or bridge arrangement) generally indicated at 142 extends between the straight portions 112 and 128. The reroute conveyor system 142 operates to transfer the article carriers (20 in FIG. 1) from the straight portion 128 to the straight portion 112 and to rotate the article carriers through an angle of 180° during the transfer from the straight portion 128 to the reroute conveyor system. The transfer occurs after the first side of the articles in the article carriers has been irradiated by the operation of a first conveyor system 139 in transporting the articles past the radiation source 10. When the transfer is made from the reroute conveyor system 142 to the first conveyor system 139, the first conveyor system transports the articles 18 past the radiation source 129 to obtain an irradiation of the second side of the articles by the radiation source 129.

A chamber 146 envelopes the conveyor system 100. The chamber may be made from a suitable radiation shielding material such as concrete. The chamber 146 is spaced from the conveyor system 100. Radiation shielding members 150 may extend between the conveyor system 100 and the radiation shielding chamber 146. The members 150 may be made from a suitable material such as steel or aluminum. The members 150 may respectively extend at an oblique angle between corners of the chamber 146 and the curved portions 118 and 122 of the conveyor system 100. Plates 152 made from a suitable radiation shielding material such as steel or aluminum may be disposed adjacent external walls of the chamber 150 to provide additional radiation shielding.

Because of the radiation shielding provided by the radiation shielding material 132 and the rods 134 and by the radiation shielding material 146 and the members 150 and 152, radiation shielding material does not have to be disposed in the vicinity of the reroute conveyor system 142. This significantly simplifies the construction of the reroute conveyor system 142. The reroute conveyor system 142 is also significantly simplified because of its minimal length between the straight portions 112 and 128. Radiation shielding material also does not have to be provided at the loading station 108 or the unloading station 110.

Figure 7:
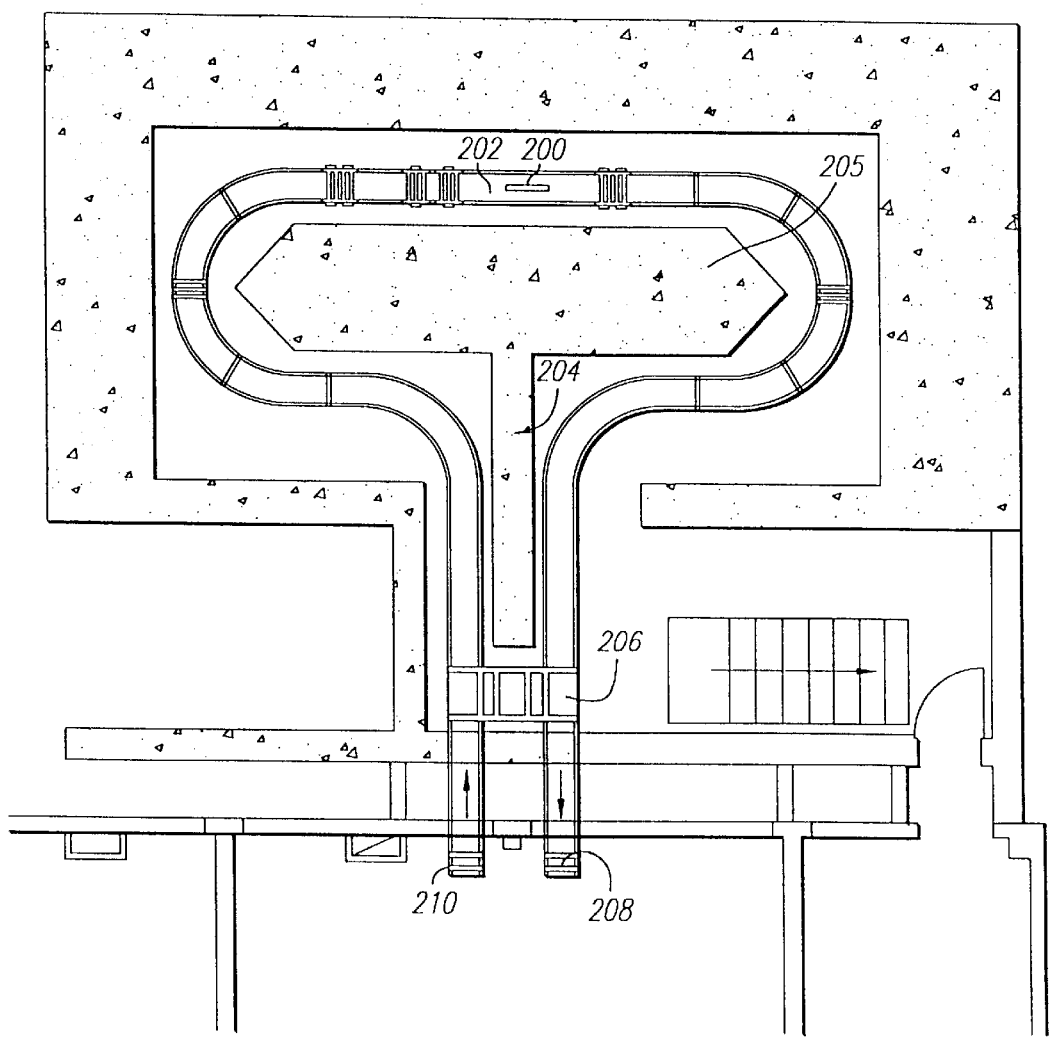
FIG. 7 is a plan view of another preferred embodiment of an irradiation system included within the scope of the invention and incorporating features shown in the previous Figures.

FIG. 7 shows another embodiment of the invention. In this embodiment, a radiation source 200 is disposed in a direction substantially perpendicular to the conveyor system 100. The radiation source 200 extends into a target region 202 to direct radiation into the articles in a direction substantially perpendicular to the plane of movement of the articles.

The embodiment shown in FIG. 7 may have radiation shielding similar to that shown in FIG. 6 and described above. However, a member corresponding to the member 134 may not be provided in the area within the conveyor system 100. Furthermore, a tongue 204 made from a suitable material such as concrete may extend from concrete material 205 in the loop within the conveyor system 100 toward a reroute conveyor system 206 corresponding to the reroute conveyor system 142 in FIG. 5. The tongue 204 operates to further prevent any radiation from the source 200 from reaching the reroute conveyor system 206 and a loading area 208 and an unloading area 210.

While the above description contains many specificities, these should not be construed as limitations on the scope of the present invention, but rather as examples of the preferred embodiments described herein. Other variations are possible and the scope of the present invention should be determined not by the embodiments described herein but rather by the claims and their legal equivalents.

What is claimed is:

1. An article irradiation system, comprising, a target region, a radiation source positioned for scanning the target region, a loading area, an unloading area, a conveyor system for transporting articles in a loop from the loading area through the target region to the unloading area, the conveyor system having curved portions, there being space within the loop and space outside of the loop, radiation shielding material disposed in the space within the loop and in the space outside of the loop to define a tunnel through which the conveyor system extends between the loading and unloading areas, the tunnel defined by the radiation shielding material at positions displaced from the target region in directions toward the loading area, and toward the unloading area, being curved to preclude a direct line of sight between the target region and each of the loading and unloading areas and thereby shield the loading and unloading areas from radiation derived from the radiation source, the space within the loop being substantially filled by the radiation shielding material.

2. An article irradiation system as set forth in claim 1, comprising, the curved potions of the loop defined by the conveyor system having opposite ends and straight portions of the conveyor system extending from the opposite curved ends of the loop, the loading and unloading areas being disposed opposite each other, and in contiguous relationship to each other, in the straight portions of the conveyor system extending from the opposite curved ends of the loop.

3. An article irradiation system as set forth in claim 1, comprising, the radiation shielding material within the loop constituting a first radiation shielding material, and a rod made from a second radiation shielding material and disposed in the space within the first radiation shielding material in the space within the loop.

4. An article irradiation system as set forth in claim 2 wherein the article has first and second sides, comprising, the conveyor system constituting a first conveyor system and providing for an irradiation of the first side of the article by the radiation source, a second conveyor system having opposite ends connected to the straight portions of the conveyor system extending from the opposite curved ends of the loop, the second conveyor system being operative to turn the article by 180° and to transfer the article to the first conveyor system for irradiation by the radiation source of the second side of the article, the second conveyor system being free of radiation shielding material and being free of radiation from the radiation source.

5. An article irradiation system as set forth in claim 4, comprising, the loading and unloading areas being disposed in a substantially contiguous relationship to each other at the straight portions of the conveyor system extending from the opposite curved ends of the loop, the loading and unloading areas being disposed further from the opposite curved ends of the loop than the second conveyor system.

6. An irradiation system as set forth in claim 5 wherein the conveyor system has curved portions and straight portions extending between the curved portions and wherein the loading area, the unloading area and the first and second conveyor systems are disposed in a particular plane and wherein the radiation source is disposed in the substantially particular plane and wherein the radiation shielding material disposed in the space within the loop is constructed to provide a reinforcement in the radiation shielding at the junctures between the curved portions and the straight portions of the conveyor system.

7. An irradiation system as set forth in claim 5 wherein the loading area, the unloading area and the first and second conveyor systems are disposed in a particular plane and wherein the radiation source is disposed in a plane substantially perpendicular to the particular plane and wherein the radiation shielding material disposed in the space outside of the loop defines a chamber having corners and wherein radiation shielding material extends between the corners of the chamber and the curved portions of the conveyor system.

8. An article irradiation system, comprising, a target region, a radiation source positioned for scanning the target region, a loading area, an unloading area, a conveyor system for transporting articles in a loop from the loading area through the target region to the unloading area, there being space within the loop and space outside of the loop, radiation shielding material disposed in the space within the loop and in the space outside of the loop to define a path through which the conveyor system extends between the loading and unloading areas, the radiation shielding material in the space within the loop and in the space outside of the loop including first and second radiation shielding materials, the first radiation shielding material providing a stronger radiation shielding than the second radiation shielding material, the first and second radiation shielding materials being disposed in the space outside the loop in a displaced relationship to each other and to the conveyor system, the path defined by the radiation shielding material at positions displaced from the target region in directions toward the loading area, and toward the unloading area, being curved to preclude a direct line of sight between the target region and each of the loading and unloading areas and thereby shield the loading and unloading areas from radiation derived from the radiation source, the curved portions of the loop defined by the conveyor system having opposite ends and straight portions of the conveyor system extending from the opposite curved ends of the loop and wherein the loading and unloading areas being disposed in a substantially contiguous relationship to each other in the straight portions of the conveyor system extending from the opposite curved ends of the loop and being free of radiation and radiation shielding material.

9. An article irradiation system as set forth in claim 8 wherein the first radiation shielding material is a metal and the second radiation shielding material is a non-metal.

10. An article irradiation system as set forth in claim 9 wherein the curved portions of the loop defined by the conveyor system have opposite ends and straight portions of the conveyor system extend from the opposite curved ends of the loop and wherein the loading and unloading areas are disposed in contiguous relationship to each other in the straight portions of the conveyor system extending from the opposite curved ends of the loop.

11. An article irradiating system as set forth in claim 9 wherein the articles have first and second opposite sides and wherein the conveyor system constitutes a first conveyor system and provides initially for an irradiation of the first side of the article by the radiation source and wherein a second conveyor system is operatively coupled to the first conveyor system to receive the article, after the irradiation of the first side of the article, to rotate the received article through an angle of 180° and to transfer the rotated article to the first conveyor system for an irradiation of the second side of the article by the radiation source and wherein the second conveyor system is disposed relative to the first conveyor system and the radiation shielding material to be free of any radiation from the radiation source and to be free of any radiation shielding material.

12. An article irradiation system as set forth in claim 11 wherein the loading and unloading areas are disposed relative to the conveyor system to be free of any radiation shielding material and to be free of any radiation.

13. An article as set forth in claim 12 wherein the radiation source, the loading and unloading areas and the first and second conveyor systems are disposed in a substantially common plane and wherein the conveyor system has curved portions and straight portions between the curved portions and wherein the radiation shielding material is shaped to provide a reinforcement in the radiation shielding at the junctures between the curved portions and the straight portions of the conveyor system.

14. An article irradiation system as set forth in claim 12 wherein the loading and unloading areas and the first and second conveyor systems are disposed in a substantially common plane and wherein the radiation source is substantially perpendicular to the substantially common plane and wherein the radiation shielding material in the space outside of the loop defines a chamber having corners and wherein the conveyor system has curved portions and wherein radiation shielding material extends between the corners of the chamber and the curved portions of the conveyor system.

15. An article irradiation system, comprising, a target region, a radiation source positioned for scanning the target region, a loading area, an unloading area, a conveyor system for transporting articles in a loop from the loading area through the target region to the unloading area, there being space within the loop and space outside of the loop, radiation shielding material disposed in the space within the loop and in the space outside of the loop to define a path through which the conveyor system extends between the loading and unloading areas, the radiation shielding material in the space outside of the loop including first and second radiation shielding materials, the first radiation shielding material providing a stronger radiation shielding than the second radiation shielding material, the second radiation shielding material disposed in the space outside of the loop being closer to the loop than the first radiation shielding material disposed in the space outside of the loop, the path defined by the radiation shielding material at positions displaced from the target region in directions toward the loading area, and toward the unloading area, being curved to preclude a direct line of sight between the target region and each of the loading and unloading areas and thereby shield the loading and unloading areas from radiation derived from the radiation source.

16. An article irradiation system as set forth in claim 15, comprising, the first radiation shielding material constituting a metal and the second radiation shielding material constituting a non-metal.

17. A system as set forth in claim 15 wherein the curved portions of the loop defined by the conveyor system have opposite curved ends and straight portions of the conveyor system extend from the opposite curved ends of the loop and wherein the loading and unloading areas are disposed opposite each other in the straight portions of the conveyor system extending from the opposite curved ends of the loop and are disposed in a substantially contiguous relationship to each other and are free of radiation shielding material.

18. A system as set forth in claim 15 wherein the article has first and second opposite sides and wherein the conveyor system constitutes a first conveyor system and provides initially for an irradiation of the first side of the article by the irradiation system and wherein a second conveyor system is operatively coupled to the first conveyor system to receive the article, after the irradiation of the first side of the article, to rotate the received article through an angle of 180° and to transfer the rotated article to the first conveyor system for an irradiation of the second side of the article by the radiation source and wherein the second conveyor system is disposed relative to the first conveyor system and the radiation shielding material to be free of any radiation from the radiation source and to be free of any radiation shielding material.

19. A system as set forth in claim 17 wherein the article has first and second opposite sides and wherein the conveyor system constitutes a first conveyor system and provides initially for an irradiation of the first side of the article by the irradiation system and wherein a second conveyor system is operatively coupled to the first conveyor system to receive the article, after the irradiation of the first side of the article, to rotate the received article through an angle of 180° and to transfer the rotated article to the first conveyor system for an irradiation of the second side of the article by the radiation source and wherein the second conveyor system is disposed relative to the first conveyor system and the radiation shielding material to be free of any radiation from the radiation source and to be free of any radiation shielding material and wherein the second conveyor system extends between the straight portions of the first conveyor system and wherein the straight portions of the first conveyor system are disposed in a substantially contiguous relationship to each other.

20. A system as set forth in claim 18 wherein the radiation source, the loading and unloading areas and the first and second conveyor systems are disposed in a substantially common plane and wherein the first conveyor system has curved portions and straight portions between the curved portions and wherein the radiation shielding material in the space outside of the loop defines a chamber having corners and wherein radiation shielding material extends between the corners of the chamber and the curved portions of the first conveyor.

21. A system as set forth in claim 18 wherein the radiation source, the loading and unloading areas and the first and second conveyor systems are disposed in a substantially common plane and wherein the radiation source is substantially perpendicular to the substantially common plane and wherein the first conveyor system has curved portions and straight portions between the first portions and wherein the radiation shielding material provides a reinforcement in the radiation shielding at positions between the curved portions and the straight portions of the first conveyor system and wherein the radiation shielding material in the space within the loop substantially fills the loop.

22. A system for irradiating articles having first and second sides, including, a radiation source constructed to provide radiation, a loading area displaced from the radiation source, an unloading area displaced from the radiation source and the loading area, a first conveyor system movable in a path, curved at particular positions along the path to define a loop, from the loading area past the radiation source to the unloading area and constructed to carry the articles in the looped path past the radiation source for an irradiation of the first side of the articles by the radiation source, radiation shielding material disposed at particular positions along the path of movement of the articles in the loop, including the curves at the particular positions along the path between the radiation source and the unloading area, and between the loading area and the radiation source, to prevent radiation from the source from reaching the loading and unloading areas, and a second conveyor system connected, between the opposite sides of the loop defined by the first conveyor system, at positions which do not receive radiation from the source, the second conveyor system being connected to the first conveyor system to receive the articles from the first conveyor system at a position after the irradiation of the first side of the article by the source and to rotate the articles through a particular angle and to transfer the articles to the first conveyor system at a position before the irradiation of the articles by the radiation source to obtain an irradiation of the second side of the articles by the source, the second conveyor system being free of radiation and radiation shielding material.

23. A system as set forth in claim 22 wherein the loading and unloading areas are free of radiation shielding material and wherein the loading and unloading areas are disposed relative to the first conveyor system to be free of radiation from the radiation source.

24. A system as set forth in claim 22 wherein the first conveyor system has straight portions extending from the curved positions to the loading and unloading areas and wherein the second conveyor system and the loading and unloading areas are connected to the first conveyor system at the straight portions of the first conveyor system and wherein the second conveyor system is closer to the curved positions in the first conveyor system than the loading and unloading areas.

25. A system as set forth in claim 20 wherein there is space within the loop and space outside of the loop and wherein the radiation shielding material is disposed in the space within the loop and in the space outside of the loop and wherein the radiation shielding material substantially fills the space within the loop.

26. A system as set forth 25 wherein the first conveyor system has straight portions between the curved portions of the first conveyor system and wherein there is space within the loop and space outside of the loop and wherein the radiation shielding material is disposed in the space within the loop and in the space outside the loop and wherein the radiation shielding material is shaped to reinforce the radiation shielding at the junctures between the curved portions and the straight portions of the conveyor system.

27. A system for irradiating articles having a first side and a second side opposite the first side, including, a radiation source constructed to provide radiation, a first conveyor system movable in a loop past the radiation source and constructed to carry the articles from a position in front of the radiation source to a position past the source for the irradiation of the first side of the articles by the radiation source, a loading area disposed relative to the first conveyor system to provide articles to the first conveyor system, an unloading area disposed relative to the first conveyor system to receive articles from the first conveyor system, a second conveyor system connected within the loop to the first conveyor system between a position past the radiation source and a position in front of the radiation source and constructed to receive the articles from the first conveyor system after the irradiation of the first side of the articles by the source and to rotate the received articles through an angle of substantially 180° and to transfer the rotated articles to the first conveyor system for the movement of the articles past the radiation source to obtain an irradiation of the second side of articles by the radiation source, radiation shielding material disposed relative to the first conveyor system and the second conveyor system and the loading and unloading areas for isolating the second conveyor system and the loading and unloading areas from the radiation from the source without any radiation shielding material at the loading or unloading areas or at the second conveyor system, and, the second conveyor system being free of radiation and the loading and unloading areas being free of radiation.

28. A system as set forth in claim 27 wherein the loop defined by the first conveyor system includes a pair of straight portions displaced from the radiation source and disposed in a substantially contiguous relationship to each other and wherein the second conveyor system is connected between the pair of the straight portions and wherein the loading area is at one of the straight portions and the unloading area is at the other one of the straight portions and wherein the loading and unloading areas are disposed in a substantially contiguous relationship to each other and wherein the loading and unloading areas are displaced further from the radiation source than the second conveyor system.

29. A system as set forth in claim 27 wherein there is space within the loop and space outside of the loop and wherein the radiation shielding material is disposed in the space within the loop and in the space outside of the loop at positions relative to the loading and unloading areas and the second conveyor system to prevent radiation from the source from reaching the second conveyor system and the loading and unloading areas and wherein the loading and unloading areas and the second conveyor system are free of radiation and radiation shielding material and the loading and unloading areas are disposed in substantially contiguous relationship to each other.

30. A system as set forth in claim 28 wherein there is space within the loop and space outside of the loop and wherein the radiation shielding material is disposed in the space within the loop and in the space outside of the loop to prevent radiation from the source from reaching the second conveyor system and the loading and unloading areas and wherein the loading and unloading areas and the second conveyor system are free of radiation shielding material and the loading and unloading areas are disposed in substantially contiguous relationship to each other.

31. A system as set forth in claim 30 wherein the radiation shielding material in the space within the loop comprises first and second radiation shielding materials and the first radiation shielding material provides a greater radiation shielding than the second radiation shielding material and wherein the first radiation shielding material is disposed within the second shielding material in the space within the loop and wherein the radiation shielding material in the space within the loop substantially fills the space within the loop.

32. A method of irradiating articles, including the steps of:

providing a radiation source, providing a loading area, providing an unloading area, providing a target region for receiving radiation from the source, providing a particular path in a loop for a movement of the articles from the loading area in the particular path through the target region to the unloading area, the particular path in the loop having configurations at particular positions in the particular path to inhibit radiation from the source from reaching the loading area and the unloading area, there being space within the loop and space outside of the loop, providing radiation shielding material at the particular positions in the space within the loop to prevent radiation from the source from reaching the loading area and the unloading area, the radiation shielding material being disposed in the particular path in the space within the loop and in the space outside of the loop and the radiation shielding material in the space within the loop substantially filling the space within the loop, and providing for a movement of the articles through the particular path in the loop to obtain an irradiation of the articles by the source in the target region.

33. A method as set forth in claim 32 wherein the radiation sealing material in the space within the loop comprises first and second radiation shielding materials, the first radiation shielding material providing a greater shielding than the second radiation shielding material, the first radiation shielding material within the loop being disposed within the second radiation shielding material within the loop.

34. A method as set forth in claim 32, including the steps of:

the articles having first and second opposite sides, the particular path constituting a first particular path, and coupling a second particular path, at a position in the loop where there is no radiation, to the first particular path to provide for a transfer of the articles from the first particular path to the second particular path after the irradiation of the first side of the articles by the radiation source, a rotation of the transferred article through an angle of substantially 180° and a transfer of the rotated articles to the first particular path for an irradiation of the second side of the articles by the radiation source, the second particular path being disposed relative to the radiation source and the radiation shielding material within the loop to be free of radiation and radiation shielding material.

35. A method as set forth in claim 34 wherein the second particular path is closer to the radiation source than the loading area and the unloading area and wherein the loading and unloading areas are disposed relative to the radiation source and the radiation shielding material within the loop to be free of radiation and radiation shielding material.

36. A system for irradiating articles, including, a target region, a radiation source positioned for scanning the target region, a loading area for the articles, an unloading area for the articles, a conveyor system disposed in a loop for transporting articles from the loading area through the target region to the unloading area, the loop being shaped to define a space within the loop, radiation shielding material substantially filling the space within the loop to prevent radiation from the source from reaching the loading area and the unloading area, the loading area and the unloading area being free of radiation shielding material and being free of radiation.

37. A system as set forth in claim 36 wherein the conveyor system constitutes a first conveyor system and wherein the articles have first and second sides and wherein the first conveyor system initially moves the articles past the radiation source to irradiate the first side of the articles and wherein a reroute conveyor system is disposed between the radiation source and the unloading and loading areas and is coupled to the first conveyor system to transfer the articles from a position on the first conveyor system past the radiation source to a position on the first conveyor system in front of the radiation source for a subsequent movement of the articles by the conveyor system past the radiation source to provide for an irradiation of the second side of the articles by the radiation source and wherein the loading area and the unloading area are disposed in substantially contiguous relationship to each other.

38. A system as set forth in claim 37 wherein the reroute conveyor system is disposed relative to the loop to minimize the distance of the reroute conveyor system and wherein the reroute conveyor system is free of radiation and radiation shielding material.

39. A system for irradiating articles as set forth in claim 37 wherein the loop has curved portions and wherein the curved portions of the loop have opposite ends and wherein straight portions of the conveyor system extend from the opposite curved ends of the loop and wherein the loading and unloading areas are disposed in a substantially contiguous relationship to each other in the straight portions of the conveyor system extending from the opposite curved ends of the loop.

40. A system as set forth in claim 39 wherein the radiation shielding material in the space within the loop includes concrete and includes a metallic rod within the concrete and wherein the loop includes curved portions and straight portions between the looped portions and wherein the radiation shielding material within the loop is shaped to reinforce the radiation shielding at the junctures between the curved portions and the straight portions of the loop.

41. A system as set forth in claim 36, including, radiation shielding material outside the loop defining a chamber having corners, the radiation source and the conveyor system being disposed within the chamber and there being space within the chamber not occupied by the radiation source and the conveyor system, the loop including curved portions, and radiation shielding material extending from the corners of the chamber to the curved portions of the loop.

42. A system as set forth in claim 37 wherein the loop has curved portions and straight portions between the curved portions and wherein the radiation source, the loading and unloading areas, the conveyor system and the reroute conveyor system are disposed in a substantially common plane and wherein the radiation shielding material is shaped to provide reinforcements at the junctures between the curved portions and the straight portions of the loop.

43. A system as set forth in claim 38 wherein the loading and unloading areas and the conveyor system and the reroute conveyor system are disposed in a substantially common plane and wherein the radiation source is substantially perpendicular to the substantially common plane and wherein the reroute conveyor system is free of radiation and radiation shielding material.

44. A system for irradiating articles having first and second sides, including, a target region, a radiation source positioned for scanning the target region, a loading area for the articles, an unloading area for the articles, the unloading area being disposed in a substantially contiguous arrangement to the loading area and being spaced from the target region and the radiation source, a first conveyor system disposed in a loop for transporting articles from the loading area past the target region to the unloading area to obtain an irradiation of the first side of the articles by the radiation source, the loop having curved portions with opposite ends and there being straight portions at the opposite ends of the curved portions, radiation shielding material disposed relative to the loop for shielding the loading area and the unloading area from the radiation source, and a reroute conveyor system disposed between the loading area and the target region to transfer to the first conveyor system the articles moving toward the unloading area after being irradiated by the source and to position the transferred articles for movement by the first conveyor system and to obtain an irradiation of the second side of the articles during the movement of the articles by the first conveyor system, the reroute conveyor system having opposite ends coupled to the straight portions of the first conveyor system, the reroute conveyor system and the loading and unloading areas being free of radiation and radiation shielding material.

45. A system as set forth in claim 44 wherein there is a space within the loop and wherein the radiating shielding material is disposed in the space within the loop for shielding the loading area and the unloading area and the reroute conveyor system from radiation from the radiation source without any radiation shielding material at the loading area or the unloading area or the reroute conveyor system.

46. A system as set, forth in claim 44 wherein the radiation shielding material substantially fills the space within the loop and wherein radiation shielding material is also disposed in the space outside of the loop.

47. A system as set forth in claim 44, including, the radiation shielding material outside of the loop defining a chamber, the radiation source and the first conveyor system being disposed within the chamber and there being within the chamber space not occupied by the radiation source and the first conveyor system, and the loading and unloading areas being disposed opposite each other and in contiguous relationship to each other in the straight portions of the conveyor system extending from the opposite curved ends of the loop.

48. A method of irradiating articles having first and second opposite sides, including the steps of:

providing a radiation source in a target region, providing a loading area, providing an unloading area in a substantially contiguous relationship to the loading area for a transfer of the articles from the unloading area to the loading area, providing a movement of the articles in a loop from the loading area through the target region to the unloading area to obtain an irradiation by the source of the first side of the articles, the loop having curved portions and defining a space within the loop, providing radiation shielding material in the space within the loop to produce, within the loop, spaces free of radiation at positions between the target region and the loading and unloading areas, and disposing a reroute conveyor system, free of radiation shielding material and free of radiation, at one of the spaces, free of radiation, between the target region and the loading and unloading areas to provide for a transfer of the articles from the loop at a position past the irradiation of the articles to a position in the loop in front of the irradiation of the articles for the irradiation of the second side of the articles by the radiation source, the loading area and the unloading area also being disposed at positions free of radiation and radiation shielding material.

49. A method as set forth in claim 48, including the steps of:

the loop having opposite ends and having straight portions at its opposite ends, the reroute conveyor system extending between the straight portions at the opposite ends of the loop, and the loading and unloading areas being disposed between the straight portions of the loop at positions further removed from the target region than the reroute conveyor system.

50. A method as set forth in claim 48, including the step of:

substantially filling the space within the loop with the radiation shielding material.

51. A method as set forth in claim 48, including the step of:

disposing the radiation source, the loading area, the unloading area, the loop and the bridging arrangement within a chamber made from a radiation shielding material and spaced from the loop and wherein the loop has curved portions and straight portions between the looped portions and wherein the radiation material within the loop is shaped to reinforce the radiation shielding at the junctures between the curved portions and the straight portions.

52. A method as set forth in claim 50 wherein the loop has curved portions and has straight portions between the curved portions and wherein the radiation shielding material is shaped to provide reinforcements in the radiation shielding at the junctures between the curved portions and the straight portions in the loop.

53. A method as set forth in claim 48 wherein the radiation shielding material substantially fills the space within the loop and wherein radiation shielding material is disposed outside of the loop to define a chamber having corners and wherein radiation shielding material extends from the corners to the curved portions of the loop.

54. A method of irradiating articles having first and second sides, including the steps of:

conveying the articles in a loop having a space within the loop, transferring the articles to the loop from a loading area free of radiation shielding material, transferring the articles from the loop to an unloading area free of radiation shielding material, irradiating the articles during the movement of the articles in the loop, and disposing radiation shielding material within the loop to shield the loading area and the unloading area against radiation, the loading area and the unloading area being free of radiation and radiation shielding material.

55. A method as set forth in claim 53 wherein the radiation shielding material includes a first radiation shielding material substantially filling the loop and a second radiation shielding material embedded in the first radiation shielding material.

56. A method as set forth in claim 53 wherein the loop has curved portions and straight portions between the curved portions and wherein the radiation shielding material within the loop is shaped to reinforce the radiation shielding at the juncture between the curved portions and the straight portions.

57. A method as set forth in claim 53, including the steps of:

providing the loop with curved portions and with straight portions between the curved portions, the straight portions being respectively disposed before and after the irradiation of the articles in the direction of movement of the articles in the loop, and providing a reroute conveyor system between the straight portions before and after the irradiation of the articles in the direction of movement of the articles in the loop, the reroute conveyor system being free of radiation and radiation shielding material.

58. A method as set forth in claim 54, there being straight portions at the ends of the loop, the loading and unloading areas being disposed opposite each other, and in contiguous relationship to each other, in the straight portions of the conveyor system at the ends of the loop.

59. A method as set forth in claim 58 wherein the radiation shielding material includes a first radiation shielding material substantially filling the loop and a second radiation shielding material embedded in the first radiation shielding material and providing a greater radiation shielding than the first radiation shielding material and wherein the loop has curved portions and straight portions between the curved portions and wherein the radiation shielding material within the loop is shaped to reinforce the radiation shielding at the juncture between the curved portions and the straight portions and wherein the straight portions are respectively disposed before and after the irradiation of the articles in the direction of movement of the articles in the loop and wherein a reroute conveyor system is provided between the straight portions before and after the irradiation of the articles in the direction of movement of the articles in the loop and wherein the reroute conveyor system is free of radiation and radiation shielding material.

\* \* \* \* \*

UNITED STATES PATENT AND TRADEMARK OFFICE
CERTIFICATE OF CORRECTION

PATENT NO. : 6,285,030 B1
DATED : September 4, 2001
INVENTOR(S) : Colin Brian Williams et al.

It is certified that error appears in the above-identified patent and that said Letters Patent is hereby corrected as shown below:

Column 12,
Line 53, change "108", to read -- 106 --.

Signed and Sealed this

Sixteenth Day of July, 2002

Attest:

Attesting Officer

JAMES E. ROGAN
Director of the United States Patent and Trademark Office